United States Patent [19]

MacApline et al.

[11] Patent Number: 4,727,196

[45] Date of Patent: Feb. 23, 1988

[54] PRODUCTION OF HIGHER CARBONYL COMPOUNDS FROM LOWER ALCOHOLS

[75] Inventors: Derek K. MacApline; Bruce L. Williams; Peter S. Williams, all of North Humberside, England

[73] Assignee: BP Chemicals Limited, London, England

[21] Appl. No.: 916,488

[22] PCT Filed: Dec. 19, 1985

[86] PCT No.: PCT/GB85/00593

§ 371 Date: Aug. 22, 1986

§ 102(e) Date: Aug. 22, 1986

[87] PCT Pub. No.: WO86/04057

PCT Pub. Date: Jul. 17, 1986

[30] Foreign Application Priority Data

Jan. 3, 1985 [GB] United Kingdom ............... 8500107

[51] Int. Cl.$^4$ .................................................. C07C 45/45
[52] U.S. Cl. ..................................... 568/391; 568/396; 568/403; 568/406
[58] Field of Search ................. 568/391, 396, 403, 406

[56] References Cited

U.S. PATENT DOCUMENTS

| 3,361,828 | 1/1968 | Robbins et al. | 568/391 |
| 3,574,763 | 4/1971 | Wollner et al. | 568/396 |
| 3,781,307 | 12/1973 | Chabardes et al. | 568/391 |
| 3,953,517 | 4/1976 | Schmitt et al. | 568/396 |
| 4,339,606 | 7/1982 | Huang et al. | 568/396 |
| 4,551,556 | 11/1985 | Nishihowa et al. | 568/403 |
| 4,562,296 | 12/1985 | Hargis | 568/403 |
| 4,567,004 | 1/1986 | Blank et al. | 568/396 |

FOREIGN PATENT DOCUMENTS

| 960007 | 3/1957 | Fed. Rep. of Germany | 568/391 |
| 1325911 | 8/1973 | United Kingdom | 568/391 |
| 2103649 | 2/1983 | United Kingdom | 568/391 |

*Primary Examiner*—James H. Reamer
*Attorney, Agent, or Firm*—Brooks Haidt Haffner & Delahunty

[57] ABSTRACT

Higher carbonyl compounds are prepared from $C_1$ to $C_8$ cyclic or acyclic alcohols containing at least one active hydrogen atom bonded to the beta carbon atom or readily convertible thereto under the reaction conditions by reacting the alcohol in the presence as catalyst of ruthenium metal or an oxide thereof supported on a solid support.

15 Claims, No Drawings

PRODUCTION OF HIGHER CARBONYL COMPOUNDS FROM LOWER ALCOHOLS

This invention relates in general to the upgrading of oxygenated compounds. In one aspect, the invention relates to the preparation of higher carbonyl compounds from lower alcohols, and optionally lower carbonyl compounds, in the presence of a ruthenium supported catalyst. In another aspect, the invention relates to the upwarding of lower alcohols to higher alcohols in the presence of the same ruthenium supported catalyst.

Catalytic dehydrogenation, hydrogenation and condensation reactions are well known. More particularly, the one step conversion of alcohols such as isopropanol into ketones such as methyl isobutyl ketone has been widely reported.

It has now been found that carbonyl compounds can be prepared by reacting lower alcohols, optionally with lower carbonyl compounds, in the presence of a ruthenium metal or metal oxide supported catalyst.

In accordance with the present invention, a process is provided for the preparation of higher carbonyl compounds from $C_1$ to $C_8$ cyclic or acyclic alcohols containing at least one active hydrogen atom bonded to the beta carbon atom or readily convertible thereto under the reaction conditions, the process comprising reacting the alcohol in the presence of a catalyst at elevated temperatures characterised in that the catalyst is ruthenium metal or an oxide thereof supported on a solid support.

The alcohols of this invention are saturated $C_1$-$C_8$ cyclic or acyclic alcohols containing at least one active hydrogen atom bonded to the beta carbon atom or readily convertible thereto under the reaction conditions employed. Examples of alcohols include but are not limited to methanol, ethanol, propanol, butanol pentanol, hexanol or combinations thereof.

The alcohols may also be reacted with lower carbonyl compounds to produce the higher carbonyl compounds. Useful lower carbonyl compounds are ketones or aldehydes having from 1 to 4 carbon atoms such as dimethyl ketone (acetone), ethyl methyl ketone, formamide, and the like.

In another embodiment of the present invention, the alcohol used in the above reaction to produce higher carbonyl compounds can be replaced by a lower carbonyl compound and a suitable amount of hydrogen. For example, in the preparation of methyl isobutyl ketone, isopropanol can be replaced with a suitable mixture of acetone and hydrogen. The ratio of lower carbonyl compound to hydrogen can vary from 3:1 to 1:1.

Provided that there is present an alcohol having at least one active hydrogen atom bonded to the beta carbon atom, other reactants need not contain an active hydrogen atom.

The higher carbonyl compounds prepared in accordance with this invention are aldehydes or ketones having at least one more carbon atom than the longest carbon chain alcohol or lower carbonyl compound reactant employed. These aldehydes and ketones may be saturated or unsaturated compounds and may be mono- or poly-aldehydes or ketones. The preferred higher carbonyl compounds produced herein are $C_4$ to $C_{10}$ saturated monoketones. Most preferred are methyl isobutyl ketone and diisobutyl ketone.

Higher alcohols, that is alcohols having at least one additional carbon atom than the reactant alcohol, may also be formed to a greater or lesser extent, depending on the nature of the alcohol reactant, the nature of the catalyst support and the reaction conditions employed.

The higher alcohols can be any alcohols having at least one additional carbon than the lower alcohol reactant. For example, ethanol can be converted into a higher alcohol such as propanol or butanol. While the higher alcohols will contain at least one additional carbon atom than the lower alcohol reactant, preferably the higher alcohol will contain 2 or more additional carbons. Butanol is the most preferred higher alcohol.

The catalysts useful in the reactions of the present invention are ruthenium metal and metal oxide supported catalysts. Suitable supports are any solid support matrix which is either acidic or basic and having the ability to catalyse condensation reactions.

The preferred condensation supports used herein are the conventional aluminas, silicas, alumina-silicas or zeolites known to those skilled in the art. The zeolite supports can range from the naturally occurring zeolites such as onalcite, chabazite, heulandite, natrolite, stilbite, or thomsonite or the artificially prepared zeolites such as X, Y or Linde type L. The preferred zeolites are the highly acidic zeolites such as alkali metal ion-exchanged X and Y zeolites.

It is also possible to use synthetic crystalline aluminosilicates having a high, that is greater than 12:1, silica to alumina ratio, for example ZSM-5 as described in U.S. Pat. No. 3,702,886, the contents of which are incorporated herein by reference.

The zeolite supports can be selected to provide some shape selectivity towards certain products. For example, NaY was found to give low amounts of is propanol from the reaction of acetone and hydrogen. However, 13 X zeolite was found to give large amounts of isopropanol in the same reaction.

The catalysts of this invention can be prepared by any conventional technique for incorporating metals into an inorganic support such as by impregnation or coprecipitation or by ion exchange techniques. The loadings can vary from about 0.1% to about 20% by weight, preferably from 3% to 10% by weight metal, based on the weight of the support.

The supported ruthenium catalysts of this invention can be promoted with alkali or alkaline earth metals. These promoter metals can be present in amounts from 0.01% to 10% by weight.

The temperatures and pressures used in these reactions can vary widely depending on the products desired. Generally, temperatures of greater than 100° C. and preferably from 150° C. to 300° C. are suitably employed. The pressures employed are typically ambient although pressures ranging from 0.1 bar to about 50 bar can be employed.

The space velocity, defined as volume of liquid phase reactants per volume catalysts per hour, can also range widely. Typically, space velocities from about 0.1 to 5 are suitable with space velocities from 0.5 to 1.0 being preferred.

When the alcohols are reacted with lower carbonyl compounds, the ratio of the respective reactants can vary widely. For example, the ratio of alcohol to lower carbonyl compound can range from 10:1 to 1:10 with a ratio of 3:1 to 1:3 being preferred.

The inventive process can be conducted in any suitable reactor in either the fluid-bed or fixed-bed mode.

Moreover, the reaction can be either a continuous or batch-type operation.

One particular advantage of using the ruthenium supported catalyst is their ability to be reactivated by contacting the catalyst with water, preferably in the gaseous phase, air or hydrogen.

When the catalyst begins losing activity (becomes spent), its activity can be reinstated by contacting it with water, air or hydrogen at temperatures from between 100° C. and 400° C. for a period of between 1 and 300 minutes. In this manner, the catalyst used in the various embodiments of this invention can maintain high levels of activity over prolonged periods.

Alternatively, steam may be co-fed to the process on a continuous or intermittent basis for the purpose of improving the catalyst lifetime.

The following Examples will further illustrate the process of the present invention. These examples have been provided to illustrate the present invention and not as limitations on the scope of this invention. It should be understood that modifications to the reactant conditions and catalysts may be made while still remaining within the scope of this invention.

PREPARATION OF HIGHER CARBONYL COMPOUNDS

All products are reported in weight percents.

EXAMPLE 1

A commercially obtained ruthenium on an alumina support containing 5% by weight ruthenium (12.6 gms) catalyst was placed in a glass tube in an oven equipped with temperature controller and the oven temperature was maintained at 180° C. Isopropanol was pumped to a preheater at a rate of 2.6 ml/h where it was volatilised and mixed with nitrogen supplied at a rate of 30 ml/minute. Condensible products leaving the reactor were trapped in an ice/water condenser.

After 3.1 hours, the isopropanol feed was stopped and the liquid product was recovered. It was found to comprise two layers of approximately equal weight and each was analysed using standard gas chromatography techniques and a Karl-Fischer water titration apparatus. All percentages are calculated by weight. The lower layer was found to contain approximately 45% water, 30% acetone, 15% isopropanol, 7% methyl isobutyl ketone (MiBK), 2% diisobutyl ketone (DiBK) and 1% 4-methylpentan-2-ol. The upper layer was found to contain approximately 34% acetone, 13% isopropanol, 30% methyl isobutyl ketone, 3% 4-methylpentan-2-ol and 17% diisobutylketone.

EXAMPLE 2

The experimental procedure of Example 1 was followed except that isopropanol was replaced by a 1.97:1 molar mixture of methanol and acetone. The liquid feed rate was 2.56 ml/hr and the nitrogen gas flow rate was 31.2 ml/minute. The liquid feed was stopped after 3.28 hrs. Analysis of the condensate showed it to contain approximately 2.5% isopropanol, 2.5% methyl ethyl ketone and 1.4% mesityl oxide.

PREPARATION OF HIGHER ALCOHOLS

EXAMPLE 3

The experimental procedure of Example 1 was followed, except that only 8.0 g of catalyst were used and the isopropanol was replaced by ethanol. The liquid feed rate was 2.5 ml/h, and the nitrogen gas feed rate was 30 ml/minute. The liquid feed was stopped after 2.3 hours. Analysis of the condensate showed it to contain approximately 7.0% n-butanol, 0.3% n-butanal, and small amounts of acetaldehyde, diethyl ether and ethyl acetate.

CATALYST REGENERATED WITH STEAM

EXAMPLE 4

The experimental procedure of Example 1 was followed except that only 2.5 g of catalyst were used. The liquid feed rate was 1.7 ml/hr and the nitrogen gas flow rate was 35.3 ml/minute. The condensed products were analysed at hourly intervals. After 12 hours, the level of MiBK had dropped from 4.8% to 1.1%. The catalyst was regenerated in situ at 330° C. by feeding water into the reaction apparatus at 1.8 ml/hr and nitrogen as at 10 ml/minute for 2 hours. After cooling under nitrogen the same reaction conditions as above were employed. The yield of MiBK increased to 16.8%.

CATALYST REGENERATED WITH HYDROGEN

EXAMPLE 5

The experimental procedure of Example 4 was followed. After 12 hours the level of MiBK had dropped from 4.4% to 1.2%. The catalyst were regenerated in situ at 230° C. by feeding hydrogen gas into the reaction apparatus at 35.3 ml/minutes for 2 hours. After cooling under hydrogen the same reaction conditions as Example 4 were employed. The yield of MiBK increased to 18.9%.

PREPARATION OF HIGHER CARBONYL COMPOUNDS WITH LOWER CARBONYL COMPOUNDS AND HYDROGEN

EXAMPLE 6

The experimental procedure of Example 1 was followed except that only 2.5 g of catalyst were used. The catalyst was treated in situ at 230° C. with hydrogen gas 35.3 ml/minute for 2 hours prior ot use. The ispropanol was replaced by acetone and the nitrogen by hydrogen. The liquid feed rate was 1.8 ml/hr and the hydrogen gas flow rate was 3.33 ml/minute. Analysis of the condensed products after 2.25 hours showed it to contain 52.6% acetone, 2.0% isopropanol, 28.6% MiBK, 0.7% mesityl oxide, 0.57% 4-methylpentan-2-ol and 8.2% diisobutyl ketone with the balance consisting of water and minor components.

PREPARATION OF ZEOLITE CATALYSTS $RuCl_3.3H_2O$ (1 g) was dissolved in distilled water (500 ml) to give a dark brown solution of pH 2.4. To this stirred solution was added NaY (Si:Al ratio=2.43:1; 4g). Stirring was continued for 2 hours over which period the pH rose to 3.9 and settled at 3.5. The zeolite was filtered, washed with distilled water until washings were free of chloride ions and dried at 80° C. for 18 hours to give the product as a black powder.

The experimental procedure of above was followed using $RuCl_3.3H_2O$ (3.3 g) in 1l of distilled water; 13X zeolite (Si:Al ratio=1.23:1; 20 g) and a reaction period of 30 minutes.

The above catalysts were activated in situ at 400° C. by treating with nitrogen, air and hydrogen. Nitrogen was passed over the catalyst at 10 l/hr for 4 hours, followed by air at 10 l/hr for 1 hour, followed by nitrogen at 10 1/hr for 1 hr, followed by hydrogen at 7 1/hr for 4 hrs. The catalysts were cooled to 180° C. under hydrogen.

EXAMPLE 7

The experimental procedure of Example 1 was followed except that the ruthenium NaY catalyst prepared and activated above (3.62 g) was used. Isopropanol was replaced by acetone and nitrogen by hydrogen. The liquid feed rate was 10 ml/hr and the hydrogen gas flow rate 20 ml/minute. The condensed products were analysed at intervals. After 2.45 hours the amount of MiBK was 3.0%, DiBK 1.7% and isopropanol (IPA) 0.0%. After 14.75 hours the acetone feed rate was reduced to 3 ml/hour. For the period 16.75 hours to 18.75 hours the amount of MiBK was 10.7%, DiBK 2.1% and isopropanol 0.3%.

EXAMPLE 8

The experimental procedure of Example 7 was followed except that the ruthenium 13X catalyst prepared and activated above (3.83 g) was used. The liquid feed rate was 10 ml/hour and the hydrogen gas flow 16.3 ml/minute. After 2 hours, the amount of MiBK was 4.6%, DiBK 1.4% and IPA 1.0%. After 5 hours the acetone feed rate was reduced to 2.5 ml/hr. For the period 8 to 10 hours the amount of MiBK was 11.1%, DiBK 1.7% and IPA 30.2%.

EXAMPLE 9

Use of Steam Co-feed to Improve Catalyst Lifetime

The catalyst of Example 5 was used. After treating with steam for 2 hours at 330° C., the level of MiBK was 17.4%.

The experimental procedure of Example 1 was followed except that isopropanol was replaced by a mixture of isopropanol and water (9:1 vol/vol) and nitrogen fed at 35.3 ml/minute. Analysis of the condensed products at intervals showed that after 17 hours the level of MiBK had dropped from 11.9% wt to 5.8% wt.

Using a similarly treated catalyst with no steam cofeed the level of MiBK dropped from 16.2% wt to 2.5% wt over 17 hours.

We claim:

1. A process for the preparation of higher carbonyl compounds from $C_1$ to $C_8$ cyclic or acylic alcohols containing at least one active hydrogen atom bonded to the beta carbon atom, the process comprising reacting the alcohol in the presence of a catalyst at elevated temperature in the range from 150° to 300° C. and at a pressure from 0.1 bar to about 50 bar, characterised in that
   the catalyst is ruthenium metal or an oxide thereof supported on a solid support, wherein the support is either an alumina, a silica, a silica-alumina or a zeolite support.

2. A process according to claim 1 wherein the alcohol is methanol, ethanol, propanel, butanol, pentanol, hexanol or combinations thereof.

3. A process according to claim 1 wherein the alcohol is reacted with a lower carbonyl compound.

4. A process according to claim 3 wherein the lower carbonyl compound is a ketone or aldehyde having from 1 to 4 carbon atoms.

5. A process according to claim 4 wherein the alcohol is replaced by a lower carbonly compound and hydrogen.

6. A process according to claim 1 wherein higher alcohols having at least one additional carbon atom than the alcohol reactant are co-produced.

7. A process according to claim 1 wherein the support is an alkali metal ion-exchanged X- or Y-type zeolite.

8. A process according to claim 1 wherein the catalyst is promoted with an alkali or alkaline earth metal.

9. A process according to claim 1 wherein the catalyst is reactivated by contacting it with air, water or hydrogen at a temperature between 100° and 400° C. for a period of between 1 and 300 minutes.

10. A process according to claim 1 wherein steam is co-fed to the process.

11. A process for the preparation of higher carbonyl compounds from compounds readily convertible under the reaction conditions into $C_1$ to $C_8$ cyclic or acyclic alcohols containing at least one active hydrogen atom bonded to the beta carbon atom, the process comprising reacting the compounds readily convertible into said alcohol in the presence of a catalyst at elevated temperature in the range from 150° to 300° C. and at a pressure from 0.1 bar to about 50 bar,
    characterised in that
    the catalyst is ruthenium metal or an oxide thereof supported on a solid support, wherein the support is either an alumina, a silica, a silica-alumina or a zeolite support.

12. A process according to claim 11 wherein the support is an alkali metal ion-exchanged X- or Y-type zeolite.

13. A process according to claim 11 wherein the catalyst is promoted with an alkali or alkaline earth metal.

14. A process according to claim 11 wherein the catalyst is reactivated by contacting it with air, water or hydrogen at a temperature between 100° and 400° C. for a period of between 1 and 300 minutes.

15. A process according to claim 11 wherein steam is co-fed to the process.

* * * * *

UNITED STATES PATENT AND TRADEMARK OFFICE
CERTIFICATE OF CORRECTION

PATENT NO. : 4,727,196
DATED : February 23, 1988
INVENTOR(S) : Derek Kenneth MacAlpine et al It is certified that error appears in the above-identified patent and that said Letters Patent is hereby corrected as shown below:

Col. 1, line 11, change "upwarding" to --upgrading--.

Col. 2, line 9, correct the spelling of "propanol".

Col. 2, line 35, "is propanol" should read -- isopropanol --.

Claim 1, line 2, correct the spelling of "acyclic".

Claim 2, line 2, correct the spelling of "propanol".

Claim 5, line 2, correct the spelling of "carbonyl".

Signed and Sealed this

Sixteenth Day of August, 1988

*Attest:*

DONALD J. QUIGG

*Attesting Officer*     *Commissioner of Patents and Trademarks*